United States Patent [19]

Robinson

[11] 4,289,850

[45] Sep. 15, 1981

[54] INTERFERON PRODUCTION

[75] Inventor: Jeffery H. Robinson, Epsom, England

[73] Assignee: Beecham Group Limited, England

[21] Appl. No.: 110,897

[22] Filed: Jan. 10, 1980

[30] Foreign Application Priority Data

Jan. 16, 1979 [GB] United Kingdom ............... 01632/79

[51] Int. Cl.$^3$ ............................................. C12P 21/00
[52] U.S. Cl. ..................................... 435/68; 435/811; 435/948
[58] Field of Search ................................. 435/68, 811

[56] References Cited

U.S. PATENT DOCUMENTS 4,007,086  2/1977  Hamilton ........................... 435/811
4,144,126  3/1979  Burbidge ........................... 435/811

Primary Examiner—Alvin E. Tanenholtz
Attorney, Agent, or Firm—Jacobs & Jacobs

[57] ABSTRACT

A method for preparing interferon in which MRC-5 cells are induced for 2 to 3 hours with an interferon-inducing medium containing from 0.1 to 50 mg $1^{-1}$ of a ds-RNA, 100 mg $1^{-1}$ of DEAE-Dextran and 250 m.M of sucrose.

Other sugars which can be used include glucose, galactose, fructose, mannose and maltose, and a preferred ds-RNA is naturally occurring ds-RNA isolated from *P. chrysogenum*.

9 Claims, No Drawings

INTERFERON PRODUCTION

This invention relates to an improved method for the production of interferon.

Interferon is the name given to glycoproteins of unknown structure which are produced by some cells in response to stimuli such as viral infection and interferon inducing agents such as natural or synthetic polyribonucleotides. The increasing importance of interferon, particularly human interferon, as a therapeutic agent in the management of viral infections such as Herpes types I and II and malignant diseases such as osteosarcoma has focused much attention on the problem of producing large quantities of interferon from cell cultures.

The production of interferon in cell culture from normal cells with the aid of a simple inducer appears to be unsatisfactory for large scale production. One solution to this problem was to use high yielding abnormal cells, since it was found that transformed and tumor cell lines often produce high interferon yields.

However, while interferon so produced may be satisfactory for non-clinical purposes it is doubtful whether material produced in this way would be acceptable for medicinal purposes.

A second solution is to try to enhance interferon yields from interferon producing cells. To date many different and indeed often conflicting methods have been suggested in the literature for improving interferon production from normal and abnormal cells. For example it has been suggested [Y. Tan et al., 1970, Proc. Natl. Acad. Sci. U.S.A., 67, 464; J. Vilcek et al., 1971, J. Virol., 7, 588, and Y. Tan et al., 1977, J. Gen. Virol., 34, 401.] that the use of inhibitors of protein and RNA synthesis such as cycloheximide combined with actinomycin D is required to enhance production of interferon from some cell lines following induction with the synthetic polynucleotide polyinosinic:polycytidylic acid (Poly I:Poly C).

The above mentioned methods for enhancing interferon production rely on causing some chemically induced physiological change in the cell. It is recognised that while specific combinations of inducer and enhancer operating in this way may be found to produce improved and high levels of interferon, but the same enhancer may be completely unable to produce satisfactory levels of interferon with another inducer. Moreover to date no discernable rule emerges from the prior art which allows one to predict with confidence how improvements to interferon yields may be obtained.

It has now been discovered that enhanced interferon production may be obtained by inducing interferon in media containing high sugar concentrations. It is thought that the enhancement is produced by a hypertonic effect and would therefore be generally applicable regardless of the interferon-inducer used.

Accordingly the present invention provides a method for preparing interferon which comprises contacting interferon-producing cells in vitro with an interferon-inducing medium comprising a non-toxic quantity of an interferon-inducing double-stranded polynucleotide, diethylamino ethyl dextran (DEAE-Dextran) and at least 100 m.mol.1$^{-1}$ of a water soluble sugar in a physiologically acceptable aqueous vehicle at physiological conditions of temperature and pH, and thereafter separating the interferon so formed.

Preferably, the sugar is a low molecular weight sugar, which is used herein to mean a pentose or hexose monomer or oligomer.

Examples of monomeric sugars (mono-saccharides) which may be used in the method of the invention are, ribose, arabinose, xylose, lyxose, allose, altrose, glucose, mannose, gulose, idose, galactose, talose, fructose, sorbose, tagatose and psicose, preferably glucose, mannose, galactose and fructose.

Examples of oligosaccharides which may be used in the method of this invention include the disaccharides, maltose, lactose and sucrose.

Preferred sugars are glucose, galactose and sucrose.

The enhancing effect commences at sugar concentrations of 100 m.molar (mM) and increases with increasing sugar concentration to peak at concentrations between 200–500 m.molar (mM).

A sugar concentration of 300–400 m.molar (mM) is preferred.

An interferon-inducing double-stranded polynucleotide means in this specification, synthetic or naturally occurring double-stranded ribonucleic acid or a double-stranded derivative thereof which is able to induce interferon.

The term "double-stranded" used in connection with ribonucleic acid refers to the characteristic wherein two ribonucleic acid molecules are associated by hydrogen bonding between complementary bases in each molecule. Ribonucleic acids may very in the degree of "double-strandedness", but the degree of double-strandedness may be determined by standard methods.

A Double-stranded derivative of a double-stranded ribonucleic acid means any double-stranded ribonucleic acid which has been subjected to a chemical or biochemical (e.g. enzymatic) reaction which alters the primary and/or secondary and/or tertiary structure, provided that the resultant derivative retains a substantial degree of base-pairing between complementary strands.

Double-stranded polynucleotides are generally recognised as falling into two categories depending upon whether they are synthetic or natural. Synthetic polynucleotides include double-stranded ribonucleic acids (ds-RNA's) such as, Poly I:Poly C, and Poly G:Poly C. Other synthetic polynucleotides are disclosed by E. De Clerq et al., J. Gen. Virol., 1977, 37, 619.

The second class of double-stranded polynucleotides are ds-RNA's of natural origin which may be isolated from virus particles occurring in virally infected strains of the fungi *P. chrysogenum, P. funiculosum, P. cyaneofulvum, P. stoloniferum, A. niger* and *A. foetidus* or from cytoplasmic polyhedrosis virus, reovirus 3 virion and the replicative form of MS2 coliphage and of MU9 mutant coliphage.

Double-stranded ribonucleic acids (ds-RNA's) of choice are those derived from *P. chrysogenum* (British Pat. No. 1170929); *P. stoloniferum* (Banks et al., Nature 1968, 218, 542); *P. cyaneofulvum* (Banks et al., Nature 1968, 223, 155); *A. niger* and *A. foetidus* (British Pat. No. 1300259).

Naturally occurring ds-RNA's are most suitable for the purpose of this invention and the ds-RNA isolated from *P. chrysogenum* is preferred.

Examples of double-stranded derivatives of ds-RNA's which may be used in the present invention but are less preferred included (the N-oxides described in our British Pat. No. 1,284,150 or the alkali-modified double-stranded ribonucleic acids in our British Pat. No. 1,356,263).

The quantity of polynucleotide is not particularly critical to this invention, and appropriate quantities may be determined by trial and error. However, in general and particularly where the preferred ds-RNA is employed low concentrations i.e. below 100 $\mu$gl$^{-1}$ produce inconveniently low quantities of interferon, and at higher concentrations for example above 100 mgl$^{-1}$ some toxic signs are observed in the cell culture. Of course the precise concentration at which the polynucleotide displays toxicity varies from cell line to cell line, and from polynucleotide to polynucleotide but in general levels which produce substantial toxic effects should not be employed. Suitable concentrations of the preferred ds-RNA lie in the range 0.1 to 50 mgl$^{-1}$ inclusive, a concentration of 1 mgl$^{-1}$ being convenient.

DEAE-Dextran is a polymer of DEAE-glucose which has a molecular weight between $10^3$ to $10^8$. DEAE-Dextran more suitable for use in the method of this invention generally has a molecular weight of $2 \times 10^4$ to $2 \times 10^6$. A number of DEAE-Dextrans of different molecular weight are available commercially, or may be made by known methods. DEAE-Dextran of molecular weight $5 \times 10^5$ as supplied by Pharmacia is particularly convenient. The concentration of DEAE-Dextran included in the induction medium will not exceed 1000 mgl$^{-1}$, 100-300 mgl$^{-1}$ being particularly convenient.

In order to put this invention into practice it is generally most convenient to culture an appropriate quantity of cells by any of the standard techniques, and thereafter to treat the cell population with the inducer in the presence of the sugar and (DEAE-Dextran).

For the purposes of in vitro propagation, cells may be considered to fall into two categories depending upon whether they may be grown in suspension or as sheets in a monolayer. The method of this invention may be applied equally to cells which grow in suspension and cells which grow in monolayers.

Typically, the suspension culture technique requires that the cells be suspended in a nutrient medium containing sources of assimilable nitrogen, oxygen and carbon, which is buffered to a physiological pH and maintained at a physiological temperature. Standard methods for growing cells in suspension are described in the standard text book Cell and Tissue Culture, J. Paul, Fourth Edition, E & S Livingstone, 1970.

The monolayer culture technique requires that the cell is anchored to some mechanical support, such as a plate or bead, and supplied with a nutrient medium as previously described by submersion or perfusion while being maintained at a physiological pH and temperature. Methods for culturing cells in monolayer are also described by J. Paul, loc. cit. Alternative methods for culturing sheet forming cells have been described by A. L. van Wezel et al., Process Biochemistry, March 1978, pp6-28; W. Wohler et al., J. Exptl. Cell Res., 74, 1972, 571; Spier, Biotech. Bioeng, 18, 649-689, 1976 and Belgian Patent No. 842002.

The method of this invention may be put into effect with either normal or transformed human or non-human cells.

Examples of suitale cells for use in this invention which grow in suspension are leucocytes, particularly peripheral blood leucocytes.

Examples of suitable sheet forming cells include epithelial cells and fibroblasts. It is also preferred to put the method of the invention into practice using sheet forming cells, in particular diploid fibroblasts.

Suitable non-human sources of cells include chicks and higher primates. However, for the purposes of producing clinical grade material it is preferred to use normal human cells and in particular MRC-5 human diploid fibroblasts.

Examples of suitable nutrient media include Eagle's, Fischer's, Ham's, Liebovitz's, McCoy's, Neumann and Tytell's, Puck's, Swim's, Trowell's or Waymouth's medium, also 199, NCTC 109, NCTC 135, CMRL 1066, or RPMI medium.

When, in the case of cells cultured by a suspension technique, a suitable population of cells is obtained, or, in the case where cells are cultured by a monolayer technique, a confluent cell sheet is obtained, the cells are contacted with the polynucleotide and DEAE-Dextran in the presence of sugar. This may be done in two ways: either an appropriate quantity of sugar followed by polynucleotide and DEAE-Dextran may be added so that the desired concentrations of sugar and polynucleotide are achieved in the nutrient medium, or the nutrient medium used for culturing the cells may be drained and replaced by an inducing medium which comprises a nutrient medium containing the appropriate levels of sugar, polynucleotide and DEAE-Dextran. The inducing medium may be prepared using any standard nutrient medium useful for cell culture as the physiologically acceptable aqueous vehicle and examples of suitable media are as described above.

The time for which the induction should be carried out will of course vary with the type of cell line employed, the concentration of inducer, sugar and DEAE-Dextran. The optimum time for any particular set of circumstances may be conveniently determined by trial and error, that is to say by titrating the interferon harvested after a series of given time periods. A period of 2 hrs. is generally preferred when using preferred quantities of the preferred inducer DEAE-Dextran and cell line.

The induction step is carried out under physiological pH conditions i.e. pH 6.5 to 8.0, and at a temperature in the range 2°-40° C., 34°-38° being most apt.

When the induction step is completed, the inducing medium is drained, optionally washed by contacting with a suitable wash medium, which may be simply phosphate buffered saline or a nutrient medium as previously described, and thereafter contacted with a harvest medium. The harvest medium is left in contact with the cells until interferon production has ceased. Suitable harvest media include phosphate buffered saline, and nutrient media as previously discussed. The length of time for which the cells are left in harvest medium depends on the length of time for which the cell continues to produce interferon. This will of course vary depending upon the type of cell which is employed, but may be determined by titrating aliquots at given time intervals.

When all interferon production has ceased, the harvest medium is drained from the cells, and the interferon recovered by standard techniques.

The following Examples illustrate the invention.

EXAMPLE 1

Induction method

MRC-5 cells were grown to confluency in 1.9 cm$^2$ wells of tissue culture plates (Linbro, FB-16-24-TC) or 8 cm² petri dishes (Nunc) using minimum essential (Eagle's) medium containing 8% foetal calf serum, 1% non-essential amino acids (Flow Laboratories), 1% penicillin-streptomycin solution (Flow Laboratories) and 2.2 .L$^{-1}$ sodium bicarbonate.

After removal of growth medium the cultures were incubated in 1.0 ml induction medium for 2 hours. Induction medium consists of minimum essential (Eagle's) medium containing 1% penicillin-streptomycin solution, 2.2 g.L$^{-1}$ sodium bicarbonate, 1 mg.L$^{-1}$ ds-RNA derived from P. chrysogenum, DEAE-Dextran (Pharmacia; 5×10⁵ mol. wt.; 100 mg.L$^{-1}$) and sucrose (200–500 mM) or another sugar as specified.

At the end of the induction period, the induction medium was removed and replaced with 1.0 ml collection medium. Cultures were incubated for a further 20 hours. Collection medium consists of minimum essential (Eagle's) medium, 1% foetal calf serum, 1% non-essential amino acids, 1% penicillin-streptomycin solution and 2.2 g.L$^{-1}$ sodium bicarbonate. At the end of this second incubation period, the interferon-containing collection medium was removed from the cultures and stored at −40° C., until assay for human interferon by a modification of the assay for chick interferon reported by Viehhauser (Viehhauser, G., (1977) *Applied and Environ. Microbiol.*, 33, 740). The amounts of interferon produced in the presence and absence of sugars are shown in Tables 1 and 2.

Assay Method

MRC-5 cells are grown to confluency in conventional roux bottles, and a cell suspension prepared by trypsinisation. The cell suspension is infected with Semliki Forest Virus, and aliquots of the suspension are dispensed into dilutions of the interferon samples (unknowns and standards) in 96-well microtitre plates. The plates are incubated for 3 days at 37° C., before fixing the cells and staining with carbol fuchsin. The end point titre is the dilution of sample which results in the cells staining to 50% of the uninfected cell control cultures. The concentration of interferon in i.u./ml is calculated by reference to the performance of the standard in the same assay.

TABLE 1*

| Sucrose enhancement in MRC-5 cells (1.9 cm² cultures) | |
|---|---|
| Induction regime | Interferon yield (i.u./ml collection medium) |
| 1 mg.L$^{-1}$ 5907 + sucrose (250 mM) | <20 |
| 1 mg.L$^{-1}$ 5907 + 100 mg.L$^{-1}$ DEAE-D | 35 |
| 1 mg.L$^{-1}$ 5907 + 100 mg.L$^{-1}$ DEAE-D + sucrose (250 mM) | 252 |

*5907 means ds-RNA derived from P. chrysogenum DEAE-D means DEAE-Dextran herein.

TABLE 2

| Sucrose, glucose and galactose enhancement in MRC-5 cells (1.9 cm² cultures) | |
|---|---|
| Induction regime | Interferon yield (i.u./ml collection medium) |
| 1 mg.L$^{-1}$ 5907 + 100 mg.L$^{-1}$ DEAE-D | 97 |
| 1 mg.L$^{-1}$ 5907 + 100 mg.L$^{-1}$ DEAE-D + sucrose (250 mM) | 566 |
| 1 mg.L$^{-1}$ 5907 + 100 mg.L$^{-1}$ DEAE-D + glucose (250 mM) | 290 |
| 1 mg.L$^{-1}$ 5907 + 100 mg.L$^{-1}$ DEAE-D + galactose (250 mM) | 260 |

Similar induction and assay methods were used in the following Examples 2 to 10.

EXAMPLE 2

A comparison of the interferon yield, in varying concentrations of sucrose, was made between MRC-5 and E4SM cells, (1.9 cm² cultures) and the results are given in Table 3.

TABLE 3

| Concentration of sucrose(mM) | Interferon yield (iu/ml) | |
|---|---|---|
| | MRC-5 | E4SM |
| 0 | 140 | 140 |
| 100 | 140 | 180 |
| 150 | 180 | 220 |
| 200 | 370 | 410 |
| 250 | 370 | 480 |
| 300 | 310 | 480 |
| 400 | 410 | 340 |

All cultures were induced for 2 hours with 5907 (1 mg.L$^{-1}$), DEAE-dextran (100 mg.L$^{-1}$) and the above indicated concentrations of sucrose.

EXAMPLE 3

A comparison of the interferon yield, in varying concentrations of sucrose, was made between MRC-5 and MRC-9 cells, (1.9 cm² cultures) and the results are given in Table 4.

TABLE 4

| Concentration of sucrose (mM) | Interferon yield (iu/ml) | |
|---|---|---|
| | MRC-5 | MRC-9 |
| 0 | 86 | 90 |
| 100 | ND | 180 |
| 250 | 330 | 210 |
| 400 | 400 | 370 |
| 500 | 210 | 250 |
| 600 | 165 | 105 |

All cultures were induced for 2 hours with 5907 (1 mg.L$^{-1}$), DEAE-dextran (100 mg.L$^{-1}$) and the above indicated concentrations of sucrose.

EXAMPLE 4

A similar method to Example 3 was used with MRC-5 and MRC-9 cells (1.9 cm² culture), but replacing sucrose with fructose. The results are given in Table 5.

TABLE 5

| Concentration of fructose(mM) | Interferon yield (iu/ml) | |
|---|---|---|
| | MRC-5 | MRC-9 |
| 0 | 85 | 90 |
| 250 | 230 | 240 |
| 400 | 490 | 340 |
| 500 | 370 | 280 |
| 600 | 300 | 220 |

All cultures were induced for 2 hours with 5907 (1 mg.L$^{-1}$), DEAE-dextran (100 mg.L$^{-1}$) and the above indicated concentrations of fructose.

EXAMPLE 5

The effect on interferon yields from MRC-5 cell cultures using different concentrations of 5907 in constant concentrations of sucrose (250 mM) and DEAE-dextran (100 mg.L$^{-1}$) was found, and the results are given in Table 6. The two experiments, 1 and 2, show the results using 8 cm² and 1.9 cm² cultures respectively.

Experiment 1 (8 cm² cultures)

| Concentration of 5907 (mg.L⁻¹) | Interferon yield (iu/ml) |
|---|---|
| 0 | <13 |
| 0.05 | 750 |
| 0.1 | 960 |
| 0.2 | 1790 |
| 0.5 | 1500 |
| 1.0 | 1370 |
| 2.0 | 1790 |
| 10.0 | 1640 |

Experiment 2 (1.9 cm² cultures)

| Concentration of 5907 (mg.L⁻¹) | Interferon yield (iu/ml) |
|---|---|
| 0.1 | 700 |
| 1.0 | 800 |
| 10.0 | 500 |
| 25.0 | 250 |
| 50.0 | 50 |
| 100.0 | 50 |

EXAMPLE 6

The effect on interferon yield from MRC-5 cells (1.9 cm² culture) using different sugars was found, and the results are given in Table 7.

Experiment 1

| Sugar | Concentration (mM) | Interferon yield (iu/ml) |
|---|---|---|
| — | — | 127 |
| Sucrose | 250 | 512 |
| Glucose | 500 | 469 |
| Galactose | 500 | 664 |
| Fructose | 500 | 862 |

Experiment 2

| Sugar Concentration (mM) | Interferon yield (iu/ml) at various Sugar concentrations (mM) | | | |
|---|---|---|---|---|
| | 0 | 300 | 400 | 500 |
| Sucrose | 102 | 208 | 190 | 208 |
| Lactose | 102 | 131 | 131 | 131 |
| Maltose | 102 | 173 | 275 | 99 |
| Fructose | 102 | 173 | 330 | 275 |
| Galactose | 102 | 158 | 228 | 330 |
| Mannose | 102 | 131 | 158 | 173 |

All cultures were induced for 2 hours with 5907 (1 mg.L⁻¹), DEAE-dextran (100 mg.L⁻¹) and the above indicated concentrations of sugars.

EXAMPLE 7

A similar method to Example 6 was used, with MRC-5 cells being replaced by MRC-9 cells (1.9 cm² cultures). The results are given in Table 8.

TABLE 8

| Sugar | Interferon yield (iu/ml) at various Sugar concentrations (mM) | | | | |
|---|---|---|---|---|---|
| | 0mM | 200mM | 300mM | 400mM | 500mM |
| Sucrose | 77 | 436 | 834 | 525 | 525 |
| Lactose | 77 | 330 | 436 | 363 | 228 |
| Maltose | 77 | 208 | 250 | 250 | 47 |
| Fructose | 77 | 363 | 693 | 436 | 275 |
| Galactose | 77 | 250 | 301 | 636 | 398 |
| Mannose | 77 | 158 | 228 | 250 | 131 |

All cultures were induced for 2 hours with 5907 (1 mg.L⁻¹), DEAE-dextran (100 mg.L⁻¹) and the above indicated concentrations of sugars.

EXAMPLE 8

The effect of varying the duration of the induction period on sucrose-enhanced interferon yields from MRC-5 cells (8 cm² cultures) was found and the results are given in Table 9.

TABLE 9

| Duration of induction (h) | Interferon yield (iu/ml) |
|---|---|
| 2 | 1879 |
| 3 | 1879 |
| 4 | 924 |
| 5 | 1318 |
| 6 | 708 |

The optimum duration of induction was found to be 2 hours.

EXAMPLE 9

The effect of varying the concentration of DEAE-dextran on sucrose-enhanced yields of interferon from MRC-5 cells was found, and the results are given in Table 10. The cells were cultured in a 1.9 cm² culture.

TABLE 10

| Concentration of DEAE-dextran (μg/ml) | Interferon yield iu/ml |
|---|---|
| 10 | 151 |
| 20 | 312 |
| 50 | 410 |
| 80 | 850 |
| 200 | 1020 |
| 500 | 312 |
| 1000 | 198 |

All cultures were induced for 2 hours with 5907 (1 μg/ml), the above indicated concentrations of DEAE-dextran and sucrose (350 mM).

EXAMPLE 10

The effect of varying the concentration of a synthetic polynucleotide (Poly I:Poly C) on sucrose enhanced interferon yields from MRC-5 cells was found, and the results are given in Table 11. The cells were cultured in a 1.9 cm² culture.

TABLE 11

| Concentration of Poly I. Poly C (μg/ml) | Concentration of DEAE-dextran (μg/ml) | Concentration of sucrose (nM) | Interferon (iu/ml) |
|---|---|---|---|
| 5 | 500 | 350 | 37 |
| 10 | 500 | 350 | 37 |
| 20 | 500 | 350 | 53 |
| 50 | 500 | 350 | 64 |
| 10 | 100 | 350 | 53 |
| 20 | 100 | 350 | 64 |

I claim:

1. A method for preparing interferon, in which interferon-producing cells are contacted in vitro with an interferon-inducing medium comprising a non-toxic quantity of an interferon-inducing double-stranded polynucleotide, diethylamine ethyl dextran (DEAE-Dextran), and at least 100 m.mol $1^{-1}$ of a water soluble sugar in a physiologically acceptable aqueous vehicle at physiological conditions of temperature and pH, and the interferon so formed is thereafter separated.

2. A method according to claim 1, wherein the amount of sugar present is from 200 to 500 m.mol $1^{-1}$.

3. A method according to claim 1, wherein the sugar is glucose, galactose, sucrose, fructose, mannose or maltose.

4. A method according to claim 1, wherein the double-stranded polynucleotide is a naturally occurring ds-RNA.

5. A method according to claim 4, characterised in that the ds-RNA is isolated from P-chrysogenum.

6. A method according to claim 1, wherein the concentration of the double-stranded polynucleotide is in the range of from 0.1 to 50 mg $1^{-1}$.

7. A method according to claim 1, wherein the concentration of DEAE-Dextran in the inducing medium is from 100 to 300 mg $1^{-1}$.

8. A method according to claim 1, wherein an appropriate quantity of cells is first cultured, and thereafter the cultured cells are treated with the interferon-inducing medium.

9. A method according to claim 8, wherein the cells are leucocytes, epithelial cells, fibroblasts or diploid fibroblasts.

* * * * *